US006217865B1

(12) United States Patent
Hunchar

(10) Patent No.: US 6,217,865 B1
(45) Date of Patent: *Apr. 17, 2001

(54) METHOD OF ANTIBODY BLENDING FOR INCREASED EFFICACY

(75) Inventor: Jeffrey G. Hunchar, West Chester, PA (US)

(73) Assignee: DCV, Inc., Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/056,690

(22) Filed: Apr. 8, 1998

(51) Int. Cl.[7] .................. A61K 39/395; A61K 35/54
(52) U.S. Cl. .............. 424/139.1; 424/581; 435/345; 530/387.1; 530/350
(58) Field of Search .................. 530/387.1, 350, 530/388.1; 424/581, 139.1; 435/345

(56) References Cited

U.S. PATENT DOCUMENTS 5,725,873 * 3/1998 Cook et al. .................... 424/424
5,827,517 * 10/1998 Cook et al. .................. 424/139.1

OTHER PUBLICATIONS

Schade et al, 1988, Biog. Amines, vol. 5, No. 6, pp. 535–550.*
Polyclonal IgY Antibodies etc., Schade et al., Institute of Pharmacology, 1040 Berlin, Germany, 1991, pp. 403–419.
IgY: Clues to the Origins of Modern Antibodies, Warr et al, Immunology Today, vol. 16, No. 8, 1995, pp. 392–398.
Immunoglobins from Egg Yolk, Akita et al., Dept. of Food Science, Vancouver BC., Journal of Food Science, vol. 57, No. 3, 1992.
Quantification & Distribution of Chicken Immunoglobins Lebacq–Verheyden et al., Univ. of Louvain, Brussels, Belgium, pp. 683–691, 1974.

* cited by examiner

*Primary Examiner*—Ali R. Salimi
(74) *Attorney, Agent, or Firm*—Basil S. Krikelis

(57) ABSTRACT

The invention relates to blending eggs from all egg lots produced over a predetermined time period of the egg laying cycle of immunized avians, to form an antibody-containing substance. The administration of an effective amount of such a blended antibody-containing substance to a subject increases the efficacy of the antibody in the subject over that of administering a substance containing the same amount of antibody obtained from eggs collected over less than the predetermined period of time.

5 Claims, No Drawings

METHOD OF ANTIBODY BLENDING FOR INCREASED EFFICACY

FIELD OF THE INVENTION

The present invention relates to a method of increasing the efficacy of an antibody in a subject. More particularly, the invention relates to blending eggs from all egg lots produced over a predetermined time period of the egg laying cycle of immunized avians, to form an antibody-containing substance. The administration of an effective amount of such a blended antibody-containing substance to a subject increases the efficacy of the antibody in the subject over that of administering a substance containing the same amount of antibody obtained from eggs collected over less than the predetermined period of time.

BACKGROUND OF THE INVENTION

The induction of an immune response in a living animal causes many things to occur within that animal, one of which is the production of antibodies. There are several characteristics of an antibody response including specificity, amount, isotype (class) and affinity of the antibodies produced. The specificity determines the ability of the antibody to distinguish one immunogen from another. The amount of antibody is a function of the number of responding B cells, their rate of antibody synthesis, and the persistence of the antibody after production. The persistence of the antibody in different tissues of the body is determined by its isotype, wherein each isotype has a different half-life in vivo. The isotypic composition of an antibody response also determines the biological functions these antibodies can perform and the sites in which they will be found. Finally, the strength of binding or affinity of the antibody to its antigen is important because the higher the affinity, the less the amount of antibody that will be necessary to eliminate the antigen.

These different characteristics of the antibodies occur at different times during the development of a mature antibody. This process is known as affinity maturation. The affinity maturation process varies not only in response to each individual immunogen, but also for every individual animal which is undergoing the immune response.

In recent years, it has been determined that avians and other animal species produce different immunoglobulins (Igs) than do mammals. In particular, mammals produce a unique series of Igs, including IgM, IgG, IgE and IgA among others. In the vertebrate classes of Amphibia, Reptilia and Aves, the primary Ig which is produced in the egg yolk is IgY. IgY is believed to be the evolutionary ancestor of IgG and IgE. Not much more, however, is known about IgY, especially with regard to its functional requirements and limitations (Warr et al., *Immunology Today*, Vol. 16, No. 8, pp 392–298, 1995).

In the art, there is a process known as passive immunization which relates to the transfer of immunity from one species to another. For example, in a common form of passive immunization, an avian is immunized with one or more immunogens. Immunization with such immunogens induces an immune response in the avian. Antibodies to the immunogens are produced by the avian during the immune response. A large number of these antibodies become concentrated in the egg of the avian. Administration to an animal of the egg containing such antibodies, or administration of the purified antibodies themselves, causes that animal to become passively immunized to the corresponding immunogens due to the transfer of the antibodies. Such a passive immunization process is the subject of U.S. Pat. No. 4,748,018, assigned to DCV, Inc. and incorporated herein by reference.

The process of passive immunization using antibodies produced in the egg of an egg-producing animal requires, of course, the collection of antibody-containing eggs from an immunized avian. In this process, it is known in the art that the highest titers of antibodies are found in eggs produced at the early stages of the egg-laying cycle of an immunized avian. As time goes on after an immune response induction, antibody titers rise quickly, eventually peak and then fall off. The production of antibody titer in the eggs of an immunized avian has been charted to generally form a bell-shaped curve over the entire egg laying-life cycle of the avian (see R. Schade et al., ATLA, 19, pp. 403–419, 1991). Antibody titers can be somewhat maintained by revaccination. Either way, it is generally the practice in the art to collect eggs soon after vaccination or revaccination (i.e. within the first few (1–5) weeks) in order to obtain eggs having the highest antibody titers.

SUMMARY OF THE INVENTION

It is an object of this invention to increase the efficacy of one or more antibodies obtained from the egg of an avian which has been immunized against one or more immunogens The efficacy of the antibodies is increased by taking all lots of eggs produced for at least the first 30 weeks following immunization, wherein all lots of eggs contain antibodies produced in response to the immunization, and blending together these lots. The blending of eggs collected over such an extended period of time results in a more efficacious antibody when administered to a subject animal.

In particular, the invention is directed to a method for increasing efficacy of an antibody in a subject comprising:

A. inducing an immune response in an egg-producing animal with at least one immunogen;

B. collecting eggs from the egg-producing animal for a predetermined period of time following induction of said immune response;

C. processing all of the collected eggs together to form a blended mix; and

D. administering to the subject a portion of the blended mix which contains an effective titer of said antibody.

The invention is additionally directed to an antibody-containing substance comprising an effective titer of at least one antibody, said antibody comprising all antibody structures produced within an animal over a predetermined period of time following induction of an immune response in said animal.

The invention is finally directed to an antibody-containing substance comprising an effective titer of at least one antibody, said antibody-containing substance comprising an egg product obtained from a blended mix of all eggs produced over a predetermined period of time by one or more egg-producing animals which have been immunized with at least one immunogen.

DETAILED DESCRIPTION OF THE INVENTION

Definitions

The term "egg or fraction thereof" means any whole egg (table, hyperimmunized or otherwise) or any product derived therefrom.

The term "egg product" refers to any substance which is produced from one or more eggs or fractions thereof.

The term "immune-egg or fraction thereof" means one or more whole eggs or any product derived therefrom, obtained from egg producing animals which have been immunized and/or maintained in an immune state.

The term "antibody-containing substance" means any substance which contains at least one antibody produced by an immunized animal.

The term "egg-laying cycle" means the entire time span over which an egg-producing animal lays eggs prior to molting.

The term "egg lot" means a mixture of eggs which are collected from one or more egg-producing animals over a specific time-period after induction of an immune response, wherein the time-period is less than the entire egg-laying cycle.

The term "blended lot of eggs" means a mixture of more than one egg lots.

The term "blended egg product" means egg product derived from a blended lot of eggs.

The term "effective amount of egg product" means an egg product containing an effective antibody titer. In particular, the amount of antibody is effective when the egg product is administered to a subject animal.

The term "hyperimmunization" means exposure to one or more antigens such that an immune response is elevated and maintained above the natural unexposed state.

The term "genetic vaccine" refers to a nucleic acid vaccine which is generally produced by recombinant technologies and which may elicit an immune response.

The term "administer" means any method of providing a subject with a substance, including orally, intranasally, parenterally (intravenously, intramuscularly, or subcutaneously), rectally or topically.

The term "animal" means any animal within the animal kingdom.

The term "target animal" refers to an animal which is immunized in order to produce an antibody-containing substance.

The term "subject animal" refers to the animal which is administered the antibody-containing substance.

The Invention

The present invention is an antibody-containing substance, and method for using the same, which comprises an effective amount of egg product obtained from a blended lot of eggs obtained from avians over a predetermined period of time following immunization with at least one immunogen. The administration of an effective amount of such a blended egg product to a subject animal increases the efficacy of the antibody over that of the same antibody obtained from eggs of immunized avians wherein the effective amount of egg product is obtained from eggs produced in less than the predetermined period of time.

Due to the premise that later formed antibodies are more mature, and as such, more effective, the inventor initially assumed that eggs produced later in the egg laying cycle would contain such mature antibodies, and an equivalent titer of antibody from such eggs would be the most effective. However, to the inventors' surprise, an effective amount of antibody from eggs collected during the weeks 15–30 following immunization was only equivalently effective to the same concentration of antibody collected from eggs produced during weeks 1–15, and not nearly as effective as that seen from an equivalent amount of antibody from eggs collected over all of weeks 1–30.

As such, the surprising aspect of this invention is that antibody obtained from a blend of eggs covering the entire time span of at least the first 30 weeks of egg production following immunization, is much more efficacious than antibody collected from portions, but not all, of the entire time span.

Immune-Egg Production

The immune egg can be produced by any egg-producing animal. It is preferred that the animal be a member of the class Aves or, in other words, an avian. Within the class Aves, domesticated fowl are preferred, but other members of this class, such as turkeys, ducks, and geese, are a suitable source of an immune egg.

When such egg-producing animals are brought to a specific state of immunization by means of, for example, periodic administrations of antigens, the animals will produce eggs which contain antibodies against those antigens.

Any immunogen or combination of immunogens may be employed as a vaccine. The immunogens can be bacterial, viral, protozoan, fungal, cellular, or any other substances to which the immune system of an egg-producing animal will respond, such as proteins and enzymes. The critical point in this step is that the immunogen(s) must be capable of inducing an immune state in the egg-producing animal. Although only a single antigen may function as the vaccine for the method of the invention, any mixture of immunogens forming a polyvalent vaccine can also be used, as is well known in the art.

Alternative vaccines that can be used to immunize the egg-producing animal include genetic vaccines. In particular, any DNA construct (generally consisting of a promoter region and an antigen encoding sequence) will trigger an immune response. Genetic vaccines consist of antigen-coding vectors, fragments of naked DNA, plasmid DNA, DNA-RNA antigens, DNA-protein conjugates, DNA-liposome conjugates, DNA expression libraries, and viral and bacterial DNA delivered to produce an immune response. Methods of DNA delivery include particle bombardment, direct injection, viral vectors, liposomes and jet injection, among others. When applying these delivery methods, much smaller quantities may be necessary and generally result in more persistent antigen production. When using such genetic processes, the preferred method for introducing DNA into avians is through intramuscular injection of the DNA into the breast muscle.

The vaccine can be either a killed or live-attenuated vaccine and can be administered by any method that elicits an immune response. It is preferred that immunization be accomplished by administering the immunogens through intramuscular injection. The preferred muscle for injection in an avian is the breast muscle. Dosage is preferably 0.05–5 milligrams of the antigenic vaccine. Other methods of administration that can be used include intravenous injection, intraperitoneal injection, intradermal, rectal suppository, aerosol or oral administration. When DNA techniques are used for the immunization process, much smaller quantities are required, generally 1–100 micrograms.

It can be determined whether the vaccine has elicited an immune response in the egg-producing animal through a number of methods known to those having skill in the art of immunology. Examples of these include enzyme-linked immunosorbent assays (ELISA), tests for the presence of antibodies to the stimulating antigens, and tests designed to evaluate the ability of immune cells from the host to respond to the immunogen. The minimum dosage of immunogen necessary to induce an immune response depends on the vaccination procedure used, including the type of adjuvants and formulation of immunogen(s) used as well as the type of egg-producing animal used as the host.

In a preferred embodiment, the immunogen used to immunize the target animal is cholecystokinin (CCK) peptide. Isolated CCK peptide has a molecular weight less than 1,500 Daltons. In order to achieve optimal immunogenicity, it is preferred that the CCK peptide be coupled chemically or through recombinant molecular techniques to larger "carrier" molecules. Examples of "carrier" molecules which make a peptide more immunogenic include ovalbumin, bovine gamma globulin (BGG), keyhole limpet hemacyanin (KLH), mouse serum albumin and rabbit serum albumin, among others. Due to its small size, it is preferred that the CCK peptide be conjugated with a carrier protein having a molecular weight of approximately 8,000 Daltons or more in order to form a conjugate of a size capable of eliciting an immune response.

A preferred method of coupling the CCK peptide to a larger protein carrier to form an immunogen is as follows. The CCK peptide is covalently coupled to a purified carrier protein, such as bovin immunoglobulin G (IgG). Electron-microscopy grade gluteraldehyde [O=CH—$(CH_2)_3$—CH=O] is preferably used as a homofunctional coupling reagent, where the aldehyde groups form an irreversible bridge between the N-terminal amino group of the peptide and the available amine groups of the protein carrier molecule. This procedure can be applied as a single step wherein the peptide is simultaneously reacted with gluteraldehyde and bovine IgG in the presence of 10 mM sodium acetate, pH 7. Glycine is then added in order to quench any unreacted aldehyde groups that may still be present. The peptide is then dialyzed and a protein assay is performed to determine the concentration of the peptide. The preparation is then preferably aliquoted and stored frozen.

Once a suitable form of the immunogen is available for immunization, it can then be used to formulate a vaccine. For example, in the case of CCK peptide, the conjugated peptide can be formulated as an adjuvant-based vaccine. This vaccine can then be used to elicit antibody production in a target animal. A typical adjuvant which can be used is Freund's complete adjuvant. If mammals comprise the target animal, then subsequent inoculations should consist of incomplete adjuvant. Other suitable adjuvants include those as referenced in *A compendium of vaccine adjuvants and excipients*, Vogel, F. R. and Powell, M. F. (1995); *In Vaccine Design, The Subunit and Adjuvant Approach*, Powell, M. F. and Newman M. J. eds Plenum Press N.Y., as well as others as are known by those having ordinary skill in the art. Amounts and concentration of adjuvant are readily determined by those having ordinary skill in the art.

In an alternative embodiment, the egg-producing animal is hyperimmunized in order to produce a supranormal level of antibodies. The hyperimmunization procedure is well known in the art, and an example is disclosed in U.S. Pat. No. 4,748,018. Having knowledge of the requirement for developing and maintaining a hyperimmune state, it is within the skill of the art to vary the amount of immunogen administered, depending on the egg-producing animal genera and strain employed, in order to maintain the animal in the hyperimmune state.

Egg Collection and Processing

Once the egg-producing animals have been sufficiently immunized to produce an immune response, it is preferred that the eggs from these animals are collected and processed into an administerable egg product.

Collection and processing of the eggs are the key elements of the present invention. As described in the background, antibodies are produced in the system of an animal during an immune response. These antibodies undergo a maturation process through time in order to develop a mature antibody which binds effectively with an immunogen to neutralize that immunogen. In other words, throughout the immune response, several antibody structures specific to a particular immunogen, are formed during the antibody maturation process. As such, eggs that are collected at different time points after the induction of an immune response will contain antibodies against the same antigen, but the antibodies will be at different stages of maturation. It is unknown in the art at what point the most effective antibody is developed, if there is such a form, and it is believed that when this form does develop, it may develop at different times post-immune response induction for each individual animal.

The essence of the invention is to mix all eggs which are collected over at least the first 30 week period following immunization. It is preferred that eggs are collected for at least 30 weeks following immunization, and as much as 100 weeks following immunization. It is more preferable that eggs are collected anywhere from 30–60 weeks following immunization.

In an alternative embodiment, eggs are collected for at least the first 30 weeks following immunization, and can be collected up until molting. Molting is a process whereby the avians stop laying eggs, and rest until the next laying cycle begins. The decision on when to molt is made by each individual egg producer.

In a preferred embodiment, eggs collected over the 30 week period are blended into a single blended lot of egg product. Once eggs laid during at least the first 30 weeks after immunization have been grouped into such a blended lot, many options are available for processing. For instance, the eggs themselves can be spray-dried or Immunoglobulin (Ig) can be separated out and purified and then an administerable antibody-containing substance can be produced. Methods for spray-drying and immunoglobulin purification are the subject of several publications and are well known in the art. Prior to administration of the antibody-containing substance, precalculated effective antibody titers, which have previously been determined, are set within these lots so th administerable fractions of the antibody-containing substances contain an effective amount of antibody therein. Once these titers are set, the administerable fraction of antibody containing substance is administered to a subject animal to passively immunize that subject animal with a more efficacious antibody.

Antibodies can be isolated and purified from animals by the methods known in the art. For instance, a number of methods for the extraction of antibodies from egg yolk have been described. Polson et al 1985 and Jensenius et al. 1981 successfully used polyethylene glycol and sodium dextran sulfate respectively as protein precipitants in the isolation of pure immunoglobulin from egg yolks. Yokoyama et al. 1992 obtained the water soluble protein fraction after the lipid components were precipitated with an aqueous dispersion of acrylic resins. Lee (U.S. Pat. No. 5,367,054, 1994) describes a high purity and high yield method for isolating and purifying immunoglobulins or fragments thereof from egg yolk by extracting the yolk with a composition containing one or more medium chain fatty acids.

Administration

An effective dose of the egg product containing an effective titer of antibody is preferably removed from the blended lot and administered to a subject animal. To the inventors' surprise, when such an amount egg product obtained from the blended lot, which contains an effective amount of antibody (i.e. a titer of antibody which is effective in inhibiting it's immunogen), is administered to a subject animal, the effect of the antibody is increased over the effect seen in those administered an effective amount of egg obtained less than all of the eggs produced over at least the first 30 weeks following immunization. Such a process has not been used in the past because, as mentioned in the background, the titer of antibody is highest in the eggs collected early (i.e. the first 1–5 weeks following -immunization), and gets lower for each subsequent lot. Therefore, the thought has always been to collect eggs soon after immunization in order to obtain the highest titers of antibody.

It is preferred that administration occur by directly feeding the egg or any derivative of the egg. The egg or egg product can be administered in a variety of ways. For example, the egg can be integrated into a food product. One preferred method for preparing the egg to be incorporated into a food product involves drying the egg into an egg powder. Although various methods are known for drying eggs, spray drying is a preferred method. The process of spray drying eggs is well known in the art. Egg is a natural food ingredients and is non-toxic and safe to those who are not otherwise allergic to eggs.

The dried egg powder can be incorporated into drinks in the form of, for example, protein powders, power building drinks, protein supplements and any other nutritional, athlete-associated products. In addition, the egg powder can be used in bake mixes, power bars, candies, cookies, etc. Other examples of egg processing include making an omelet, soft or hard-boiling the egg, baking the egg, or, if desired, the egg can be eaten raw or processed as liquid egg.

Finally, it is generally known by those having ordinary skill in the art that further separation could provide more potent fractions or elimination of undesirable components, and would allow for other modes of administration such as administering egg product parenterally, subcutaneously, intravenously, intramuscularly, intraperitoneally, intranasally, orally or topically. Such further separation will provide for the ability to make encapsulated products and pharmaceutical compositions with said egg or fraction thereof.

It is of significant importance to point out that the egg product of this invention has been shown to be safe, non-toxic, ideal for long term use and has no side effects other than on those animals which are allergic to eggs. The egg product can be orally administered either alone or in combination with drug therapy.

Alternative Embodiments

It is possible to produce and collect antibodies using the process of the invention from other sources such as milk, colostrum, whole blood, plasma and serum of the target animal. It is within the ordinary skill in the art to determine optimum minimum time periods within which to collect milk, serum, etc. to obtain the most efficacious antibody containing blend.

It is further contemplated that the invention is not limited to passive immunization.

For instance, it is contemplated that human antibodies produced in, and collected from humans over a predetermined period of time, as described by the invention, can be administered to other humans (active immunization) to increase efficacy of the antibody.

The advantageous properties of this invention can be observed by reference to the following examples which illustrate the invention.

EXAMPLES

Example 1

Eliciting CCK-8 Antibodies in Eggs

Methods

CCK-peptide vaccines were prepared by conjugation of synthetic cholecystokinin (CCK-8) (Fragment 26–33 amide with sulfated tyrosine) to bovine gamma globulin (BGG) using glutaraldehyde. The vaccines were emulsified with Freund's complete adjuvant (1:1) and injected (100 $\mu$g CCK) into laying hens. A second injection of the CCK-8 conjugate in Freund's incomplete adjuvant was injected 7 days after primary injection. A second group of control hens did not receive the CCK vaccination. Approximately 2,880 eggs were collected 5 months after the initial injection and the whole eggs were separated into egg yolk and egg white. The egg yolk was spray dried in 8 lots and the antibody titers of the blended spray dried yolk powder were measured.

Results

ELISA determinations of the CCK antibody in spray dried egg yolk showed higher end point titers when compared with negative control egg yolk (TABLE 1). Yolks from hens vaccinated with CCK-8 peptide showed an average of 1064 $\mu$g/gram in contrast to the negative control egg yolk which contained 3.4 $\mu$g/gram specific antibody against CCK-8 peptide.

TABLE 1

Analysis of Specific Anti-CCK-8 Antibody

| Sample | Average anti-CCK-8 Antibody (ug/gram yolk) | Average End Point Titer |
|---|---|---|
| Yolk from Hens Vaccinated with CCK-8 Peptide Conjugate | 1064 | 394240 |
| Negative Control Yolk | 3.4 | 3379 |

Example 2

Correlation of Blended Lots of CCK AB to Biological Activity in Broiler Chickens A total of 6552 one-day-old straight run Ross x Hubbard HyY broiler chicks was used in the experiment. There were 13 treatments with 7 replicates per treatment and 72 birds per replicate. The individual pen was the experimental unit. Blended material from thirty weeks of production was used in this project. A total of six lots were used with a lot being defined as the egg material obtained from approximately 5 weeks of production. Lot 1 was the material obtained from the first 5 weeks of production, Lot 2 was from the second 5 weeks of production, and so on with Lot 6 being from the final 5 weeks (i.e. weeks 25–30) of production.

TABLE 2

EXPERIMENTAL TREATMENTS

| Treatment | Replicates | Animals Per Pen | Grams Per Ton | Ug Of Antibody Per Ton |
|---|---|---|---|---|
| Negative Control | 7 | 72 | none | 0 |
| Lot 1 | 7 | 72 | 46 g/ton | 48,195 |
| 1050 ug/g | 7 | 72 | 54 g/ton | 56,700 |
|  | 7 | 72 | 62 g/ton | 65,205 |
| Blended Lots | 7 | 72 | 71 g/ton | 48,195 |
| 1–3 680 ug/g | 7 | 72 | 83.5 g/ton | 56,700 |
|  | 7 | 72 | 96 g/ton | 65,205 |
| Blended Lots | 7 | 72 | 220 g/ton | 48,195 |
| 4–6 230 ug/g | 7 | 72 | 244 g/ton | 56,700 |
|  | 7 | 72 | 281 g/ton | 65,205 |
| Blended Lots | 7 | 72 | 120 g/ton | 48,195 |
| 1–6 400 ug/g | 7 | 72 | 141 g/ton | 56,700 |
|  | 7 | 72 | 162 g/ton | 65,205 |

CCK antibody titers were determined for each Lot and ug of anti CCK/gm was determined from this titer. Blended lots were fed at rate to give a predicted amount of antibody in each lot.

TABLE 3

Weight Gain

| Treatment | 48,195 ug/ton | 56,700 ug/ton | 65,205 ug/ton |
|---|---|---|---|
| Negative Control | 4.566 e |  |  |
| Lot 1 | 4.599 cde | 4.621 bcde | 4.647 abcd |
| Blended Lot 1–3 | 4.596 de | 4.630 abcde | 4.683 ab |
| Blended Lot 4–6 | 4.597 cde | 4.640 abcd | 4.682 ab |
| Blended Lot 1–6 | 4.581 de | 4.666 abc | 4.694 a |

*values with the same letters are not significantly different

TABLE 4

Feed Efficiency

| Treatment | 48,195 ug/ton | 56,700 ug/ton | 65,205 ug/ton |
|---|---|---|---|
| Negative Control | 1.831 f |  |  |
| Lot 1 | 1.824 f | 1.814 ef | 1.792 bcde |
| Blended Lot 1–3 | 1.818 ef | 1.802 cdef | 1.774 ab |
| Blended Lot 4–6 | 1.814 def | 1.798 abcd | 1.774 abc |
| Blended Lot 1–6 | 1.813 def | 1.780 abc | 1.758 a |

*values with the same letters are not significantly different

Results and Conclusions

Weight gain and feed efficiency were positively affected by the blending of CCK antibody feed. Weight gain and feed efficiency were improved numerically for all doses of CCK antibody fed when compared to the negative control. Weight gain and feed efficiency improved numerically within each lot as the dose was increased. Blending of lots fed to broilers improves weight gain and feed efficiency over the negative control and the positive control (Lot 1). The results of this study indicate statistically that the blending of CCK antibody should include at least 30 weeks of production material before being used commercially in order to achieve the most benefit to performance.

What is claimed is:

1. A method for increasing efficacy of an antibody in a subject comprising
   A. inducing an immune response in an egg-producing animal with at least one immunogen;
   B. collecting eggs from the egg-producing animal for a period of time comprising 30 to 60 weeks following induction of said immune response;
   C. processing all of the collected eggs together to form a blended mix; and
   D. administering to the subject a portion of the blended mix which contains an effective titer of said antibody.

2. The method of claim 1 wherein the immonogen is selected from the group consisting of proteins, enzymes, bacteria, viruses, protozoa, fungi, cellular antigens, allergens and combinations thereof.

3. The method of claim 2 wherein the immonogen comprises cholecystokinin.

4. The method of claim 1 wherein the egg-producing animal comprises an avian.

5. The method of claim 4 wherein the avian is selected from the group consisting of fowls, turkeys, ducks and geese.

* * * * *